（12）United States Patent
Petryakov et al.

(10) Patent No.: US 10,371,780 B2
(45) Date of Patent: Aug. 6, 2019

(54) SYSTEM AND METHOD FOR POST-EXPOSURE DOSIMETRY USING ELECTRON PARAMAGNETIC RESONANCE SPECTROSCOPY OF TEETH

(71) Applicant: THE TRUSTEES OF DARTMOUTH COLLEGE, Hanover, NH (US)

(72) Inventors: Sergey V. Petryakov, Lebanon, NH (US); Wilson A. Schreiber, Hanover, NH (US); Harold M. Swartz, Lyme, NH (US); Benjamin B. Williams, Thetford Ctr., VT (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 406 days.

(21) Appl. No.: 15/187,389

(22) Filed: Jun. 20, 2016

(65) Prior Publication Data
US 2016/0370446 A1 Dec. 22, 2016

Related U.S. Application Data

(60) Provisional application No. 62/182,016, filed on Jun. 19, 2015.

(51) Int. Cl.
*G01R 33/60* (2006.01)
*G01R 33/36* (2006.01)
(Continued)

(52) U.S. Cl.
CPC .............. *G01R 33/60* (2013.01); *A61B 5/055* (2013.01); *A61B 5/4547* (2013.01); *G01R 33/341* (2013.01); *G01R 33/3628* (2013.01); *G01R 33/34007* (2013.01); *G01R 33/3642* (2013.01); *G01R 33/3685* (2013.01); *G01R 33/3802* (2013.01)

(58) Field of Classification Search
CPC .... G01R 33/60; G01R 33/36; G01R 33/3628; G01R 33/341; G01R 33/38; G01R 33/3802; G01R 33/3685; G01R 33/3642; G01R 33/34; G01R 33/34007; A61B 5/00; A61B 5/055; A61B 5/4547
See application file for complete search history.

(56) References Cited

U.S. PATENT DOCUMENTS

2004/0251899 A1* 12/2004 Swartz .................. G01N 24/10
324/316
2009/0216109 A1* 8/2009 Karmarkar ....... A61B 17/12022
600/411

(Continued)

*Primary Examiner* — Son T Le
(74) *Attorney, Agent, or Firm* — Lathrop Gage LLP (57) ABSTRACT

An apparatus and method for triaging patients according to radiation exposure operates by measuring electron paramagnetic resonance spectra of teeth. When operating in vivo, radiation induced spectra are obtained from intact teeth placed within a magnetic field and with a resonator having a loop and two capacitors formed in metal layers on a printed circuit substrate and located near teeth. The resonator is magnetically coupled to an RF measuring system. The spectra are used to determine radiation dose of a subject. The characteristics of the method and the apparatus make it feasible to utilize the system to measure radiation dose using previously untrained operators working in the field under emergency conditions.

17 Claims, 7 Drawing Sheets

(51) Int. Cl.
*A61B 5/00* (2006.01)
*G01R 33/38* (2006.01)
*G01R 33/34* (2006.01)
*A61B 5/055* (2006.01)
*G01R 33/341* (2006.01)

(56) References Cited

U.S. PATENT DOCUMENTS

| 2011/0130647 A1* | 6/2011 | Swartz | G01R 33/286 |
| | | | 600/421 |
| 2012/0112746 A1* | 5/2012 | Hyde | G01N 24/10 |
| | | | 324/316 |
| 2016/0266226 A1* | 9/2016 | Chow | G01R 33/60 |

* cited by examiner

SYSTEM AND METHOD FOR POST-EXPOSURE DOSIMETRY USING ELECTRON PARAMAGNETIC RESONANCE SPECTROSCOPY OF TEETH

CROSS-REFERENCE TO RELATED APPLICATIONS

This application claims the benefit of priority to United States Provisional Patent Application No. 62/182,016 filed 19 Jun. 2015, which is incorporated by reference herein in its entirety.

GOVERNMENT RIGHTS

This invention was made with government support under grant no. AI091173 awarded by the National Institutes of Health and under grant no. HHSO0100201100024C awarded by the Department of Health and Human Services. The government has certain rights in the invention.

FIELD

The present document relates to the field of electron paramagnetic resonance (also known as electron spin resonance) spectroscopy as applied to measuring ionizing radiation doses received by a subject.

BACKGROUND

While most molecules have paired electrons in consequence of covalent bonding, some molecules—including free radicals—have electrons that are not paired. Paired electrons have opposite spins ($M_s=+/-\frac{1}{2}$) that cancel out net magnetic moments. Unpaired electrons have spins that can interact with magnetic fields.

Unpaired electrons in molecules will resonate in a magnetic field. Electron Paramagnetic Resonance Spectroscopy (EPR), sometimes known as Electron Spin Resonance Spectroscopy, takes advantage of this effect to quantify and determine environments of the unpaired electrons. This is done by applying a magnetic field to a substance, which may be located within a human or animal subject, to align spins of any unpaired electrons in the substance. Once spins are aligned, a response of the spins of the unpaired electrons in the substance to radio-frequency electromagnetic radiation at and near a resonant frequency is measured. The resonant frequency and amount of absorption of the electromagnetic radiation is often dependent on the local environment of the unpaired electrons in the molecule as well as the applied magnetic field. The resonance results in such effects as a spike in a radio-frequency absorption spectrum of the substance in a magnetic field.

An EPR spectrum is often acquired by placing a sample in a magnetic field, holding a frequency of a radio frequency source and absorption measuring device constant, and making repeated measurements of response of the sample to the radio frequency energy while sweeping the intensity of the magnetic field. An EPR spectrum may also be obtained by repeated measurements of absorption made while holding the magnetic field intensity constant and sweeping the frequency of a radio frequency source and measuring device. The measuring device may measure spin echoes in addition to, or in place of, absorption.

Unpaired electrons are naturally found in small quantities in chemicals, such as free radicals, that are found in biological materials. For example, free radicals are produced during, and have importance in oxidative energy production by mitochondria. The amounts of these free radicals, however, are very low in unirradiated teeth and therefore will not contribute to the EPR signal detected in vivo It is known that certain hard tissues, including the hydroxyapatite in tooth enamel and keratin in fingernails, develop and retain unpaired electrons capable of producing an EPR signal when teeth and/or fingernails are subjected to ionizing radiation.

In the case of teeth, this EPR signal is roughly proportional to the mass of tooth enamel and to the total radiation dose received in that mass since the tooth formed. This radiation-induced signal has a long half-life on the order of hundreds of thousands of years.

Nuclear accidents resulting in significant radiation exposures to workers in the nuclear industry are known; for this reason many such workers carry film badges or dosimeters with which to determine their exposure in any incident. Occasionally, such as the 1945 death of Harry Dahglian, or in 1946 the death of Lewis Slotin (both exposed to the same plutonium bomb pit, which had gone critical due to erroneously placed, nearby, neutron reflecting materials), such dosimeters have been left elsewhere during an incident, or the radiation dose may exceed the range of the dosimeter—estimates of Slotin's exposure are as high as 9-11 Gray.

While nuclear reactor operators and other workers in the nuclear power and medical radiation treatment industries typically carry dosimeters for measuring radiation exposure in their work environment, members of the public, emergency services crews, and armed forces rarely carry such dosimeters. In the event of nuclear accident, terrorism, or warfare, it would be desirable to measure recent radiation exposure of people exposed to such events, including those who do not habitually carry dosimeters.

Past techniques for measuring EPR signal in teeth to determine radiation dose have required extraction of a tooth, a procedure that would not be logistically feasible with the expected victims of nuclear disasters.

In an international climate where perpetual enemies India and Pakistan are both nuclear powers, where North Korea has nuclear weapons and Iran—a country that has threatened Israel, a country widely believed to be a nuclear power—may soon acquire them, and organizations such as ISIS have threatened to smuggle and detonate either a nuclear device or a "dirty bomb", the risk of a nuclear attack or terrorism is rising. Further, with worldwide interest in nuclear power to produce electricity without emitting greenhouse gasses, there is a significant risk of nuclear accident, possibly involving off-site release of contaminants as with Chernobyl or Fukoshima. Nuclear accidents have also resulted from improper disposal of radioactive materials, such as radiation treatment machines.

In a nuclear attack, nuclear improper-disposal events, and nuclear accidents, there may be people potentially exposed to ionizing radiation while not carrying previously-issued dosimeters. Both a nuclear attack and a nuclear accident could be mass-exposure situations with several hundred to tens of thousands of people potentially exposed to radiation.

The Chernobyl, Goiânia, and Hiroshima events each involved at least some deaths from acute radiation syndrome, as have other events. Gabriella, the Brazilian scrap-metal scavenger who carried the glowing core of a radiation treatment machine across a city in a bus, not only gave herself a fatal radiation dose, but exposed others to varying and unknown doses of radiation, as did her husband and others in the family These events illustrate need for measurements of radiation exposure in potentially thousands of individuals of widely varying radiation exposure.

In mass exposure situations there are widespread serious concerns, where 'worried-well' people physically unaffected by the event may believe that their lives are in danger and therefore require methods to determine objectively that they do not have life-threatening exposures to ionizing radiation. This phenomenon is expected to occur in nuclear events such as nuclear attack, terrorism, or accident. Further, there are likely to be limited medical facilities available after some such events—treatment of everyone, the 'worried well' as well as the exposed, is not expected to be possible immediately after a major event.

It is desirable to be able to rapidly sort people into categories which may include:

those who are 'worried well,' needing no treatment;

those with minimal exposure-possibly sufficient to cause increased cancer rates or otherwise need followup-but who will not need immediate treatment for acute radiation sickness;

those who have received significant exposure but should recover from acute radiation sickness with conventional therapy such as antibiotics and transfusions;

those who should recover from acute radiation sickness with aggressive therapy such as marrow transplants; and those who will probably die regardless of treatment.

In the short term, treatment can then be focused upon those groups who most likely will benefit from the treatment. The process of sorting people according to injuries into treatable, urgently treatable, or untreatable groups is known as triage Existing technologies for determining those exposed to large doses of radiation are often based on biological responses to ionizing radiation and include changes in white blood cells, changes in levels of gene expression, changes in metabolites and changes in proteins produced. Unfortunately, not only do such measurements require skilled medical staff, but baseline levels vary among individuals, responses to radiations vary among individuals, these levels are likely to be dependent on both prior history and acute simultaneous events such as concurrent stress and trauma. Also, the biologically-based changes must vary over time as they depend on naturally occurring reactions to damage and therefore must have time-dependent changes as the responses are indicated, modulated, and then tend to return towards normal levels. Physically based biodosimetry, specifically electron paramagnetic resonance measurements of radiation-induce free radicals in the enamel of teeth, differ from the biologically based responses as being independent of prior history (except for therapeutic irradiations that include high doses to the teeth), independent of concurrent stress and trauma, and have an immediate and unchanging dose-dependent response to ionizing radiation that can be rigorously quantitated.

SUMMARY

Apparatus for performing electron paramagnetic resonance (EPR) spectrometry in teeth in vivo has a magnet having pole plates and gap sufficiently large to permit positioning a head with at least one unextracted tooth of a subject within a uniform magnetic field zone provided by the magnet; a device for positioning at least one resonator near the at least one unextracted tooth of in the in-vivo subject; a coupler configured to inductively or capacitively couple the resonator to a radio frequency measuring device adapted to determining an EPR spectra; a processing system for computing a radiation dose based upon the EPR spectra, and for measuring the radiation dose; and apparatus for outputting the triage measured radiation dose.

A method for measuring radiation dose includes placing a resonator on the incisor tooth of a subject, the resonator being inductively (magnetically) or capacitively coupled to a coupler attached to a radio frequency measuring device (RF bridge), the resonator comprising a loop and two capacitors; measuring at least one EPR spectrum of unextracted teeth of the subject in a magnetic field; and estimating radiation dose of the subject from the measured EPR spectra. Apparatus for performing electron paramagnetic resonance (EPR) spectrometry in teeth in vivo includes a magnet having sufficient space between poles for a subject's head to be rapidly and comfortably positioned between the poles; at least one resonator having a loop and two capacitors formed in metal layers on a printed circuit substrate and adapted for placement adjacent to at least one tooth of the subject; a radio frequency measuring device magnetically coupled to at least one resonator and adapted for measuring at least one EPR spectrum; a processing system for computing a radiation dose based upon the EPR spectrum, and apparatus for outputting the radiation dose.

DETAILED DESCRIPTION OF THE EMBODIMENTS

Figure 1:
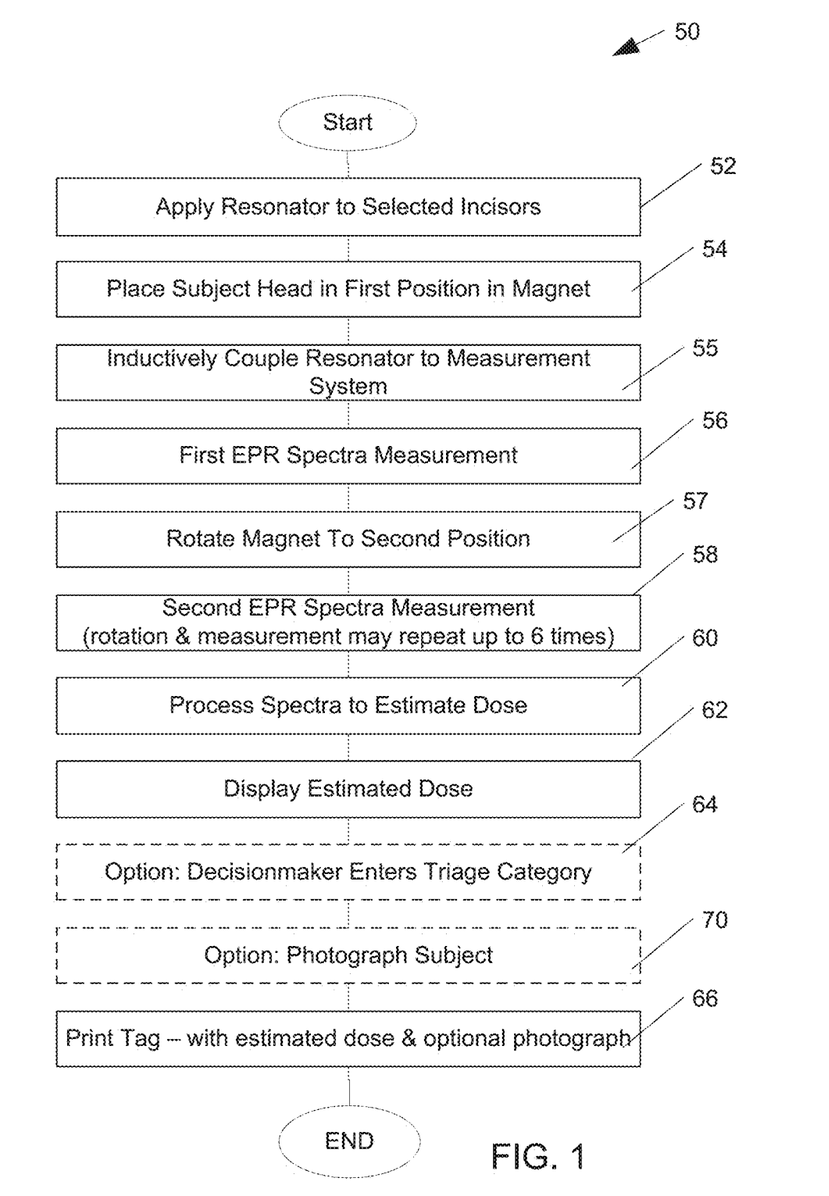
FIG. 1 is a flowchart of an in-vitro method for dosimetry by determining a radiation induced EPR signal (RIS) in teeth.
Figure 2:
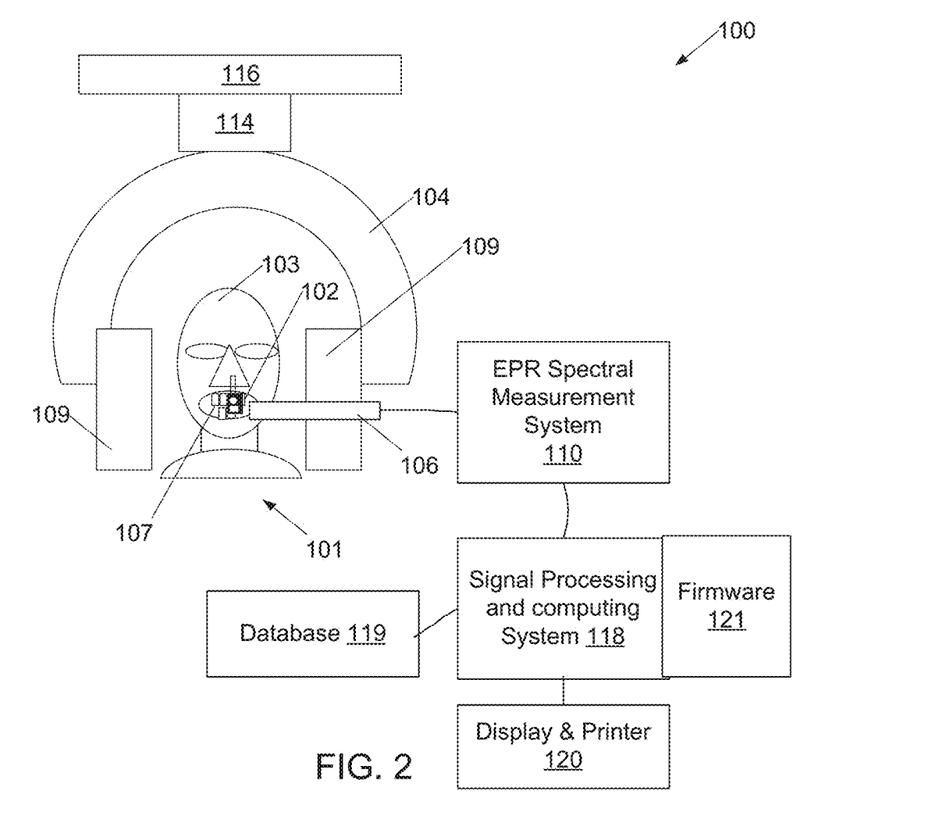
FIG. 2 illustrates a block diagram of a subject positioned in an apparatus for radiation dosimetry by measuring EPR RIS in the subject's teeth.
Figure 3:
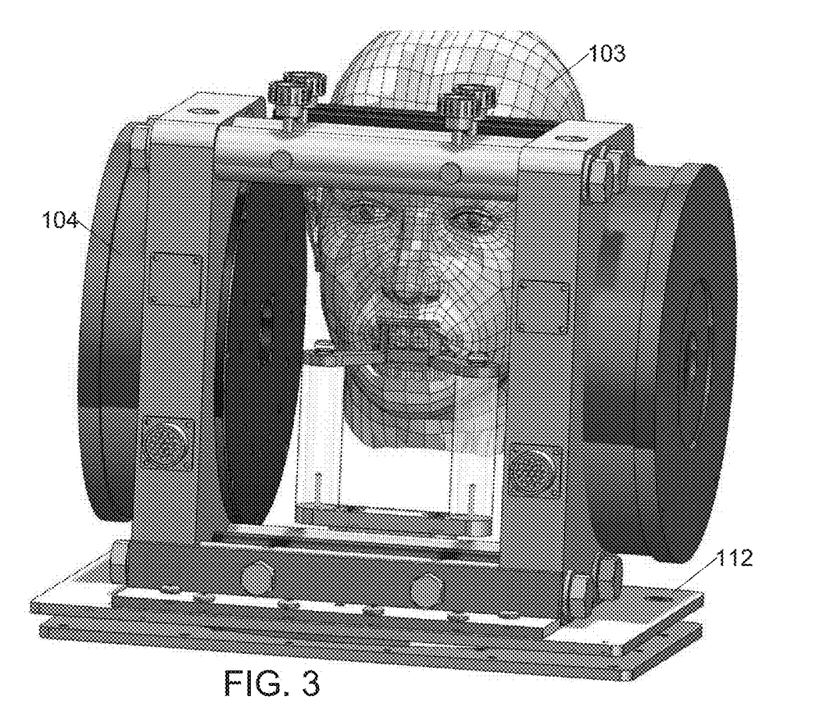
FIG. 3 illustrates an embodiment having permanent magnet mounted on a turntable.

An in-vitro method 50 of determining radiation dose experienced by a subject is illustrated in FIG. 1 with reference to the schematic apparatus 100 illustrated in FIG. 2 and FIG. 3. The method 50 begins with placing 52 a disposable resonator 102 on the subject's 101 incisor 107. The subject's head 103 is then placed 54 in a uniform magnetic field provided by a magnet 104 providing a suitable magnetic field strength, and a measurement instrument 106 is inductively coupled 55 to the resonator 102 through a coupler 108. In order to improve subject compliance, the magnet 104 has a gap and pole pieces sufficiently large that the subject's head can be positioned with teeth, including incisors, within a near-uniform field zone provided by the magnet without extracting said teeth. A first EPR spectral series is then measured 56 from the subject's incisor tooth 107 by the measurement instrument 106. All EPR spectra are transmitted to a signal processing and computing system 118. The apparatus is optionally coupled to an electronic medical record database 119 adapted to maintain medical records for subjects examined The magnet may be a permanent magnet 104 with appropriately shaped pole pieces 109 and actively driven electromagnetic coils, as shown in FIG. 3. In an alternative embodiment, the magnet is an electromagnet. In an embodiment the magnet, which may be a permanent magnet or paired electromagnets as illustrated, is mounted on a turntable 112 that permits rotation of the magnet with respect to the subject's head 103. In an alternative embodiment, the magnet is mounted from an overhead bearing 114 attached to a beam 116, the bearing permits rotation of the magnet.

The magnet is then rotated 57 to position the magnet in a second position relative to the subjects head, and a second EPR spectral series is measured 58 and transmitted to signal processing and computing system 118. The first and second spectral series are processed 60 in a signal processing system to estimate an approximate dose and thence display the dose to a decision maker 62 on a display system 120, who optionally may enter a triage category 64. In a particular embodiment, a tag appropriate to the category is printed 66 bearing the estimated dose and an identification of the subject, which in an embodiment includes a photograph of the subject, and which may include an entered triage category.

In order to minimize power requirements in a field screening device the magnet 104 may in some embodiments comprise a permanent magnet having suitable pole-pieces 109 attached to it, the magnet may also have electromagnetic coils attached to it for sweeping and modulating the main magnetic field. The magnet is mounted in a rotatable mount, which may be a turntable under the magnet as illustrated in FIG. 3 requiring the subject lean forward into the magnet, or may be suspended from an overhead bearing, as illustrated in FIG. 2, with the subject positioned beneath the magnet.

The Resonator

The sensing component of a conventional L-band (1.2 GHz) EPR spectrometer typically is a surface coil resonator and coupling structure that is rigidly, physically attached to the other components of the EPR spectrometer, which result in bulky and cumbersome operation, limitations in samples/sites to be measured, low in sensitivity, complicates requirements for cleanliness in medical applications, and hinders the overall performance and utility of the spectrometer.

Figure 4A:
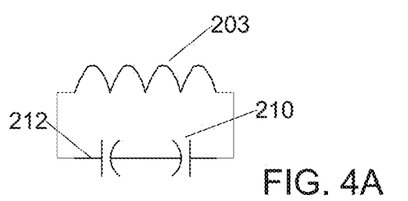
FIG. 4A is a schematic of the tooth surface resonator.
Figure 4B:
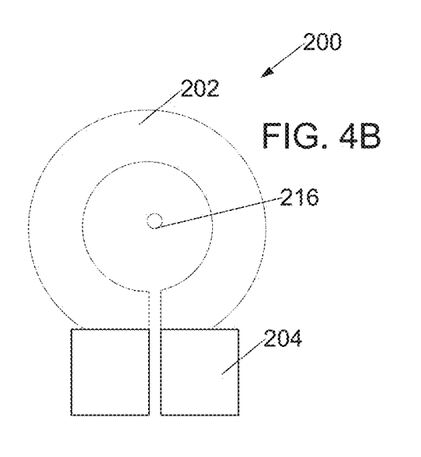
FIG. 4B is a front side printed circuit layout of the tooth surface resonator.
Figure 4C:
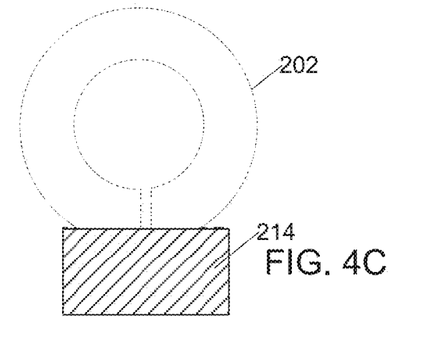
FIG. 4C is a back-side printed circuit layout of the tooth surface resonator showing some front-side layout in dashed lines.

In order to solve these issues, a removable, disposable, resonator, as illustrated in FIG. 4A, 4B, and 4C, has been developed. The removable, disposable, resonator is inductively coupled to a nearby, coupling structure 106 that is in turn electrically connected to the EPR spectral measurement system 110. While in an embodiment this coupler uses inductive coupling, in other embodiments capacitive coupling may also be used. The term AC-coupled shall include both inductively and capacitively coupled embodiments.

An exemplary removable, disposable, inductively coupled, resonator is the double-sided printed-circuit resonator illustrated in FIG. 4A in schematic form, FIG. 4B as a front side printed circuit layout, and FIG. 4C as a back-side printed circuit layout of the tooth surface resonator showing some front-side layout in dashed lines to illustrate alignment, has a loop 202 that is modeled as an inductor 203, the loop 202 contiguous with two plates 204, 206 that form plates of capacitors 210, 212, all on a front surface of the printed circuit resonator. The opposite plates of the capacitors, together with electrical connection between capacitors 212, 210, is formed as a single metal rectangle 214 on the back surface of the printed circuit resonator; capacitor dielectric is formed of the flexible printed circuit substrate. The metal shapes 202, 204, 206, 214 are formed of silver-plated copper. The resonator also has alignment holes, not shown, for positioning an inductive coupling device of coupling structure 106, and, in some embodiments an EPR reference sample 216 formed of a small sample of perdeuterated N15 tempone (PDT) within loop 202. This acts as a reference standard used for spectral fitting and discrimination of unwanted spectral features that would otherwise confound dosimetric results. The resonator is flexible in order to conform to a wide variety of sizes, shapes, and contours of an incisor tooth subjects or patients.

Figure 5A:
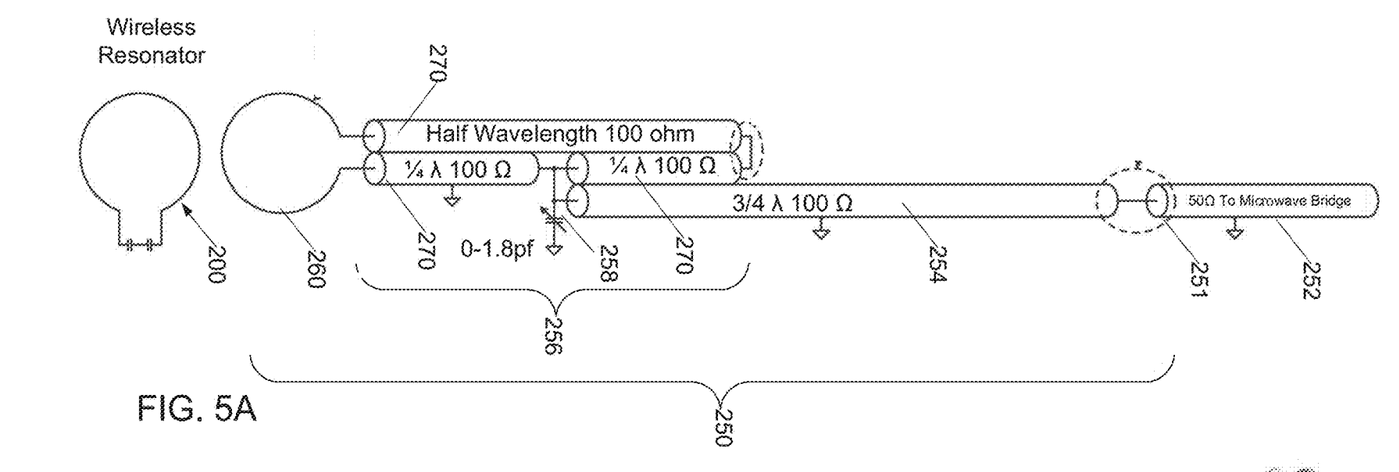
FIG. 5A is an electrical schematic and block diagram illustration of the resonator with a coupler adapted for coupling the resonator to an EPR measurement system.

Inductive coupling of the resonator 200 eliminates the need for the measurement sample, or in the case of EPR tooth dosimetry, the measurement subject, to be physically and galvanically connected to the coupler, FIG. 5A, of the EPR spectrometer. This wireless surface coil resonator is inductively coupled to an EPR bridge and spectrometer through the use of an antenna coupler 250.

Figure 5B:
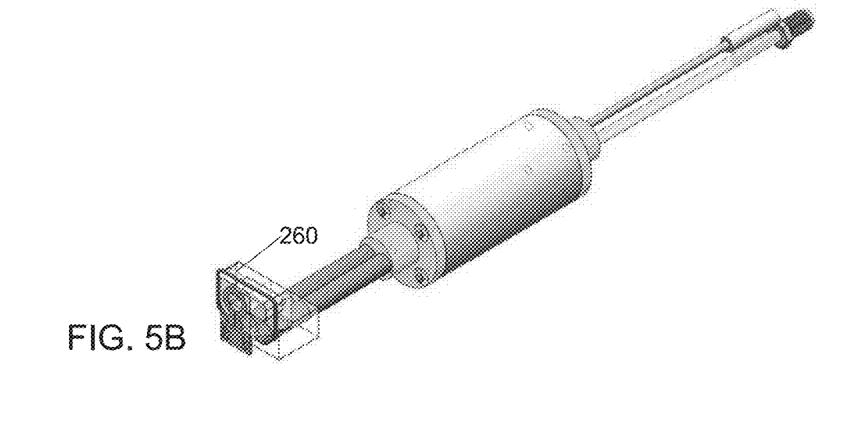
FIG. 5B is a rendering of a coupler adapted for coupling the resonator to an EPR measurement system of FIG. 5A.
Figure 6:
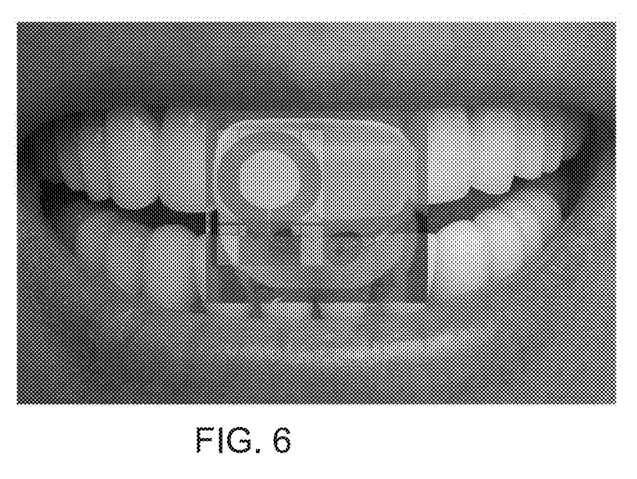
FIG. 6 is a photograph of the resonator superimposed on a photograph of subject's mouth, with the resonator positioned to measure EPR resonances of an incisor.
Figure 7:
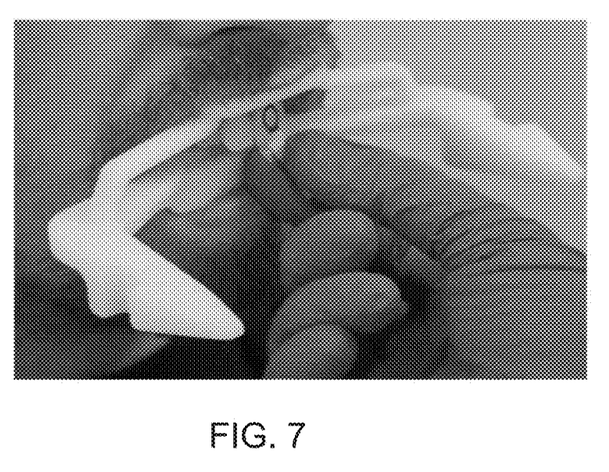
FIG. 7 is a photograph of the resonator and a mouthpiece frame adapted to position the antenna and restrain movement of the subject during EPR measurements.
Figure 8:
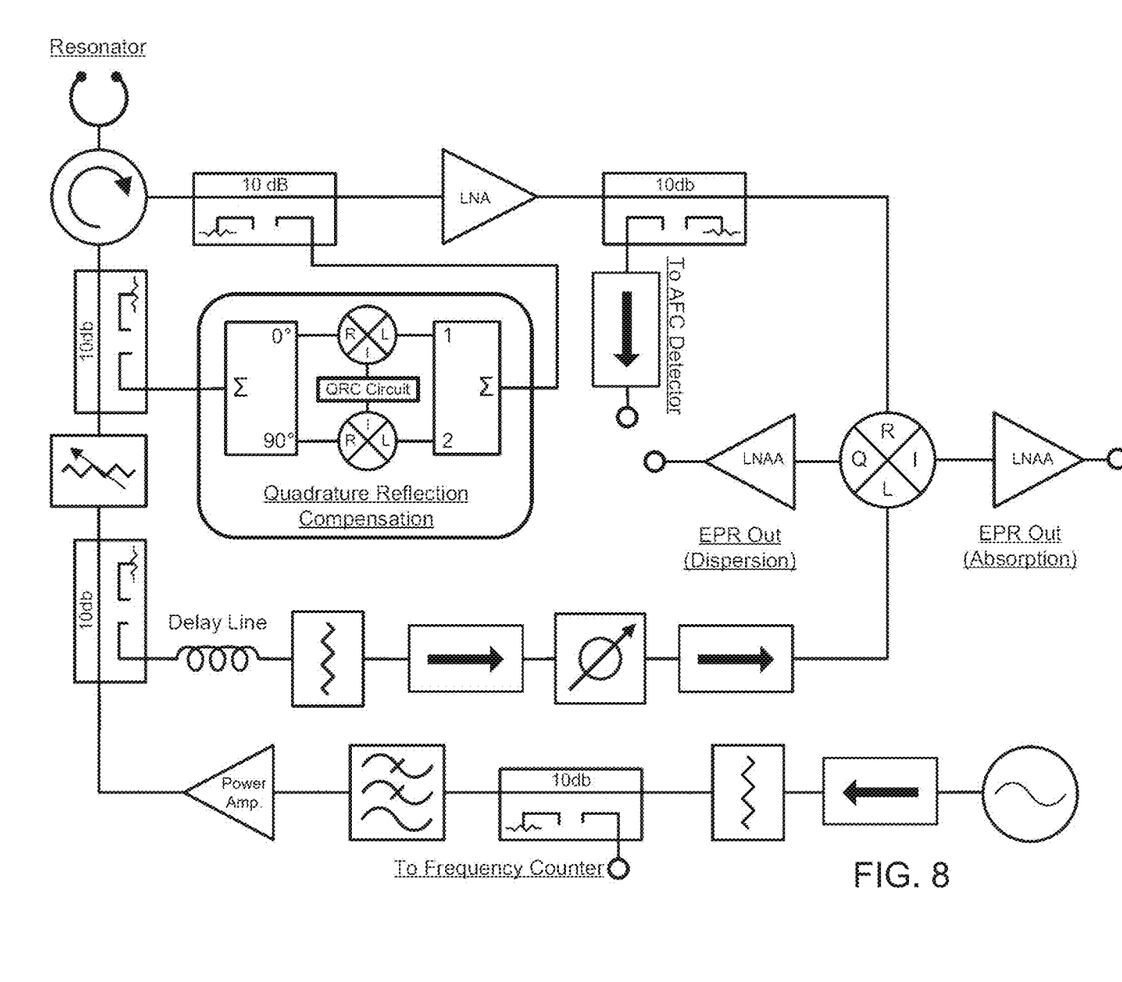
FIG. 8 is a block level diagram of the Multiple Harmonic Quadrature Homodyne Detector with Reflection Compensation used to detect EPR signals from teeth.

Antenna coupler 250 includes a connector 251 adapted to allow connection to a measurement system using a 50-ohm coaxial cable 252, an impedance matching coaxial line portion 254, a balun 256 portion, a fine-tuning coupling capacitor 258, and an antenna coil 260 adapted to couple to the resonator 200, as well as pins (not shown) adapted for mating with alignment holes (not shown) of the resonator to ensure correct positioning of resonator 200 in coupler 250 despite rapid replacement of resonators in the coupler. Antenna coil 260 in a particular embodiment is a single loop of 200-micron silver-plated copper wire approximately one-quarter wavelength long; in alternative embodiments the wire of the loop may be of other diameters small relative to the wavelength. In an embodiment, the balun 256 portion comprises an approximately half-wavelength 272 and two approximately quarter-wavelength coaxial lines, together with a coupling adjustment capacitor 274 of 0.1-8.0 picofarad (pf). The coupler is further illustrated in FIG. 5B, which illustrates a mechanical positioning device 276 located next to antenna coil 260 and adapted to hold resonator 200.

In a particular embodiment, wireless resonator 200 is fabricated of a Teflon flexible substrate (Polyflon of Norwalk, Conn.) with oxygen-free copper on either side. The profile of the wireless resonant sensor is etched into the copper cladding, and excess material removed. This is then coated with a layer of silver, with thickness on the equal to or greater than the skin depth of the frequency of the EPR resonance condition. For 1.15 GHz L-band, this skin depth is about 8 microns. Oxygen-free copper and silver plating were utilized for these wireless sensors in order to eliminate magnetic components used near/on the resonant structure, and reduce the potential of unwanted spectral baseline and spectral distortions, as well as unwanted paramagnetic centers.

We have developed a cleaning method for these materials that ameliorates virtually all unwanted baseline signals, and unwanted EPR signals. This method entails soaking these wireless sensors in a low-concentration (15% by volume) of hydrochloric acid for approximately 20 minutes, followed by three rinsing cycles in 99.9% HPLC-grade isopropanol to rid the sensor of water (from the low-concentration hydrochloric acid) and provide a hygienic preparation of the sensor for use in vivo.

The equivalent schematic of the wireless resonator as shown in FIG. 4A create a LC-resonance with its resonant frequency dictated by the capacitive divider network 210, 212 at the base of the wireless sensor. These two equal capacitors can be treated as one combined element, whose physical lengths, widths, and thickness of the dielectric substrate can be varied in to create the desired LC resonance. For L-band tooth dosimetry, this frequency is 1.15 GHz±15 MHz when the resonator is applied to a tooth—resonance frequency is higher when in free air.

In an alternative embodiment, coupler 250 balun is replaced by a transformer having a transmitting wire loop on the equipment end, and a receiving wire loop on the resonator end, the receiving wire loop in turn coupled to wire loop 260. In this embodiment the transmitting and receiving wire loops of the transformer are located coaxially, but an adjustable distance apart to permit adjustment of resonator coupling.

The Measurement System

The measurement system uses Multiple Harmonic Quadrature Homodyne Detection and Reflection Compensation (MHQHDRC)

The transitions that occur from passing a spin system through resonance result in a rich array of signals from the spin systems, but typically only those of the first harmonic typically are detected in continuous wave EPR spectroscopy. We use multiple harmonic quadrature detection for the specific purpose of improving dose estimation in little acquisition time, providing increased amounts of useful data within the same period of time. This has been implemented by utilizing quadrature down-converting mixers which are driven by an ultra-low phase noise RF source, which preserves the signal-to-noise ratio in the dispersion channel of the quadrature mixer. Multiple higher harmonics, including at least the second and third harmonics of the stimulus frequency, and in a particular embodiment the second, third, fourth, and fifth harmonics, are then extracted from the absorption and dispersion channels respectively and are fit to a spectral model which combines the multiple spectra generated by one scan resulting in less noise present in the combined resultant spectra to more accurately estimate the dose to the tooth in a lesser time.

This portion of the invention utilizes the feedback generated by the quadrature homodyne detection to provide an estimation of the imbalance/reflection (standing-wave ratio) of the resonator and RF bridge system. With these estimations, RF power can then be automatically injected back into the receiving arm of the RF Bridge at opposing (180-degree shifted) phase to effectively cancel out the detected vector of reflected power, as seen by an RF detector. Reducing or eliminating reflected RF power from the resonator to the bridge results in the maximum signal-to-noise that can be obtained for a given measurement. The introduction of this system through the refined detection methods has enabled the automation of this reflection compensation system to enable its use by either automated control software, or a minimally trained operator.

The EPR spectra are detected with lock-in amplifiers that are synchronized to the frequency and phase of the modulating magnetic field. Typically, the out-of-phase signal is phased locked to the lock-in amplifier so that 100% of the detected signal from the spins is in the in-phase channel, however this may not be practical in the field under less controlled conditions and with magnet rotation. Therefore, for each signal component (absorption and dispersion) there is an out-of-phase component that will need to be combined to the in-phase component in order to maximize signal amplitude through lock-in, phase sensitive detection. Then, the absorption and dispersion are combined in order to provide one spectra for a given harmonic. This process is repeated for n-harmonics.

1) Absorption in-phase and out-of-phase data are read into the spectral manipulation routine and any linear baselines (slopes and offsets) are removed.

2) In-phase and out-of-phase spectral data are converted into polar spectral data to manipulate the spectral phase of the in-phase and out-of-phase components collectively in order to minimize the signal content of the out-of-phase data, resulting in all EPR spectral amplitudes to be effectively transferred into the in-phase spectra, resulting in pure absorption spectra.

3) Dispersion in-phase and out-of-phase data are read into the spectral manipulation routine and any linear baselines (slopes and offsets) are removed.

4) In-phase and out-of-phase spectral data are converted into polar spectral data to manipulate the spectral phase of the in-phase and out-of-phase components collectively in order to minimize the residuals (fitted EPR spectra minus data it is fitted to) of the out-of-phase data, resulting in EPR spectral amplitudes effectively transferred into the in-phase spectra, resulting in pure dispersion spectra. At this point, the four spectra original have been converted into two spectra 5) Pure absorption and pure dispersion spectra are then processed by a Hilbert Transform routine.

6) Hilbert transform routine converts the phase of the dispersion spectra to the phase of the absorption spectra 7) Pure absorption spectra are then summed with the Hilbert-transformed dispersion spectra. At this point, the four spectra have been combined into one spectrum.

8) The summed spectra then fit to a spectral model, and then the radiation induced signal amplitude is extracted.

9) The EPR (also RF) phase is then extracted from spectral fitting, and is applied back to all four original spectra to ensure that all spectra are properly phased, within tolerance.

Steps 1-9 are repeated for n-harmonics, and combined in the same fashion to result in one fitted spectra and one dose estimation per set of scans/spectra. In a particular embodiment, four harmonics of a base 1.15 GHz L-band signal are processed. In an alternative embodiment, spectra are obtained at second and third harmonics of an L-band signal near 1.15 GHz.

Magnet Rotation for Reduction of Baseline Signals

For a given position of a resonator on a measurement sample, accuracy and precision of the measurement made using an EPR spectrometer can be adversely affected by unwanted baseline signals in the collected spectra. A physical perturbation to the measurement system is typically necessary in order to significantly change the spectral shape of the unwanted spectral features of these baseline signals. These then can be averaged out by combining data using several perturbations. Failure to remove the varying baseline signals degrades the precision of the measurements.

Prior art tooth dosimetry systems physically perturb the system by repetitively repositioning the resonator on the tooth approximately 6 times. While effective, repositioning the resonator has the considerable problem of requiring expertise or an extremely high level of automation not suitable for the intended use of the device.

We rotate the magnet to at least 3 positions relative to the subject's head, a center position, a minus-5 degree position with the magnet rotated 5 degrees to the patient's left, and a plus-5 degree position with the magnet rotated 5 degrees from the center position to the patient's right, as well as several positions in between the +−5 degree rotation, depending on the compliance of the measurement subject and time available for measurement; these positions alter the magnetic field slightly by rotating the relative static, sweeping, and modulating magnetic field accomplishes the needed perturbation in a way that can be easily automated and requires no expertise by the operator. The magnet is rotated, spectra are collected, and this process is repeated in order to utilize averaging to obtain a relevant estimation of dose in the sample/subject.

In an embodiment, magnet rotation is performed by an electric motor (not shown) coupled to rotate the magnet within a range of plus and minus five degrees from an initial alignment of magnet 104 to the subject's head 103 under direction of firmware 121 executing on signal processing and computing system 118. Plus or minus five degree rotation permits a programmable difference of between zero and ten degrees between a first angle and a second angle at which EPR spectra are obtained.

In an alternative embodiment, the magnet is rotated to three positions relative to the subject's head, a center position corresponding to an initial alignment of the magnet to the patient's head, a minus-5 degree position with the magnet rotated 5 degrees to the patient's left, and a plus-5 degree position with the magnet rotated 5 degrees from the center position towards the patient's right. EPR spectra are obtained at each of these three positions. In some embodiments, EPR spectra data is taken in as many as 6 positions of magnet relative to the subject's head.

In another alternative embodiment, only two positions are used, with the rotation angle selected between three and five degrees between the first and second position.

In another alternative embodiment, EPR spectra are obtained at a multiple of angles of magnet to head greater than three, the multiple angles selected from angles between minus five and plus five degrees relative to an initial alignment of magnet to head.

Signal Processing and Dosimetric Data Analysis

Figure 9:
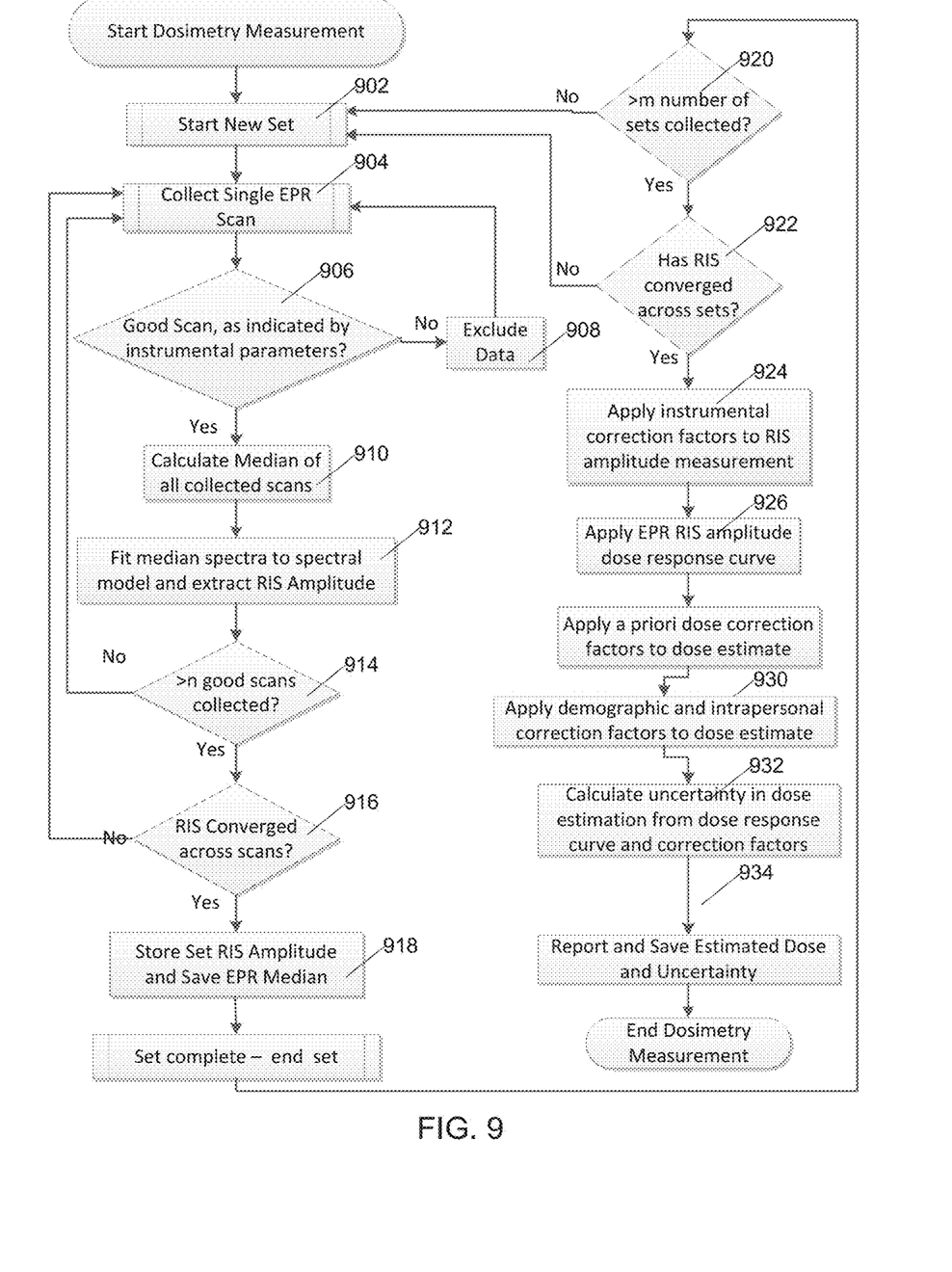
FIG. 9 is a flowchart illustrating the methodology for acquiring multiple scans and collections of scans to estimate the dose of the measurement subject and stopping data acquisition once sufficient measurement precision is obtained.

Conventionally, EPR dosimetry measurements have been based on measurement time rather than decreasing the uncertainty of the estimate of the individuals dose. Newly developed combination of data collection methods and processing analyses have enabled EPR dosimetry to collect dosimetric data that will automatically determine when further collection of data will not significantly improve the precision of that set (collection of individual scans), as illustrated in FIG. 9, so that a new set of data can immediately begin to be collected following a perturbation to the measurement system by magnet rotation. This is done by utilizing metrics and trends of dose estimation throughout the data acquisition process so the most precision is obtained within the available time. It has previously been demonstrated that more sets results in a greater precision of dose estimation as compared to simply collecting more scans. This Dynamic Adaptive Dosimetric Data Analysis enables a much more efficient use of the time available for the measurements to achieve an accurate dose estimate.

In this dynamic adaptive dosimetric data acquisition, the magnet is set to a first angular position relative to the subject's head and a count of sets of scans is cleared and a new dataset 902 is begun for each angle of magnet to subject head. An EPR spectral scan is obtained 904 by sweeping frequency or magnetic field strength, and validated 906 as a good scan meeting quality limits including several instrumental parameters including 1) reflected RF power (balance) level, 2) RF phase error, and 3) automatic frequency control (AFC) error. If the scan fails to meet requirements it is discarded 908. Each scan requires approximately three seconds. The median is calculated for each spectral point for all validated scans 912, and checked for a predetermined minimum number of scans (n) 914. Each median spectra is then fit to a spectral model, where an estimation of the radiation induced signal (RIS) amplitude is extracted, and the averaged RIS over the sequence of scans is checked for convergence 916 to within predefined criteria. Once converged, the EPR median is saved along with the RIS amplitude for a particular set of scans, and the count of sets of scans is incremented; at particular counts of scans the magnet is rotated to a next position of the positions to be used during scanning this subject. If the count of sets of scans has not reached a minimum number (m) 920, or if the RIS of median spectra of acquired sets of scans has not converged 922, a new set is started 920.

Once the RIS has converged over multiple sets and the minimum number of sets has been acquired, correction factors for the instrument are applied 924 and a dose-response curve is applied to determine 926 an absolute dose. Demographic and intrapersonal corrections are then applied 930 to give a more accurate dose estimation for that individual. A dose uncertainty range is also calculated 932. When displaying estimated dose 92 and printing the tag 66, both the calculated dose and uncertainty are displayed.

While scanning can be performed by sweeping either frequency or magnetic field across the electron resonance point, we use a coil to sweep the magnetic field by 25-gauss in three-seconds resulting in one individual EPR spectra. Three instrumental data quality metric signals are also synchronously acquired with the scan: 1) reflected RF power (balance) level, 2) RF phase error, and 3) automatic frequency control (AFC) error. A set of scans is a collection of good scans resulting in one median spectra being created from all good scans within this set. Scans whose mean value of the three instrumental data-quality signals exceeds a given threshold are ignored. A median spectra is calculated for n-spectral data points across m-scans in order to reduce the 1/f noise for a given set given a minimal number of scans (m), reduce the influence of noise spikes that enter our scan spectra and do not contribute to other instrumental data-quality metrics thresholds for data exclusion, and filter out artifacts of the observed signal that are not coherent with the repeatable sweep of our main magnetic field.

Each set (median spectra) is then fit to a spectral model, where an estimation of the radiation induced signal (RIS) amplitude is extracted for this set, which is used to estimate the dose absorbed by the measured subject.

A magnet rotation alters spectral baseline distortion that is intrinsic to EPR spectroscopy of very small EPR signals (such as those found in irradiated teeth) that otherwise confounds dosimetric measurements in order to effectively ameliorate this unwanted baseline distortion out of our dosimetric estimates to levels of precision outlined by government guidelines (0.5 Gy); separate sets are collected at each magnet position.

A collection of sets resulting in one dose estimation for a given subject, and the uncertainty in the dose estimation by the following process:

1. The mean value of the RIS (in arbitrary units) across all collected sets is calculated resulting in one dose estimation (in arbitrary units).

2. Standard error of the mean (SEM) is calculated across set means resulting in an uncertainty estimation in the dose estimation (in arbitrary units)

3. Instrumental correction factors (such as resonator quality factor correction, EPR reference standard corrections, tooth size corrections, etc.) are then applied to the RIS and SEM (in arbitrary units).

4. The RIS and SEM (with instrumental corrections applied) are then applied to a previously determined linear dose response curve to units of absorbed dose: Gray (Gy), which is defined as 1 joule of ionizing radiation absorbed per kilogram of matter.

5. Dose correction factors (such as age, demographics, etc.) and associated uncertainties are then applied to the corrected RIS (now in units of Gy).

6. Dose estimation and uncertainty are reported in units of Gy.

In an embodiment, an EPR reference standard such as a perdeuterated N15 tempone (PDT) sample is present within the magnetic field while the resonance is being measured. This sample in an embodiment is printed at the center of the resonator loop. This acts as a reference standard used as a field marker used for spectral fitting and discrimination of unwanted spectral features that would otherwise confound dosimetric results. In an alternative embodiment, a reference sample is present in a capillary tube located near the resonator.

In an embodiment, an estimated whole-body radiation dose of the subject is computed from the RIS. The estimated dose is displayed 64 in a form suitable for use by the decision-maker for determining how to triage, and a tag with the dose reading is printed 66; the tag may include a triage category entered by the decision-maker. In order to prevent measured subjects from trading tags to gain more favorable treatment than their condition warrants, in some embodiments the subject is photographed 70 and the printed tag may include the photograph of the subject.

In an alternative embodiment, once it has been determined that a subject has received at least some radiation, fingernail and toenail clippings from each hand and foot may also be analyzed in different EPR dosimeter apparatus according to a method we have previously disclosed to determine a dosage distribution across the body. Dosage distribution is of interest because bone marrow from lightly or un-irradiated limbs may provide stem cells to re-seed marrow in more intensely irradiated portions of the body, therefore identifying subjects who have received exposures that vary significantly from limb to limb may allow some of these unevenly-irradiated subjects to avoid drastic treatments like heterologous bone marrow transplantation.

In large-scale disasters, subject's recalled history alone has proven to not always be a good indicator of exposure to toxic or radioactive materials and corresponding need for treatment. Similarly, apparent physical injuries and symptoms are not good indicators of intensity of radiation doses received by a subject. When a radiation disaster, whether by accident like Chernobyl, or weapon such as the one used on Hiroshima, happens, medical care systems will likely be overloaded. In many scenarios, including use of nuclear weapons, many subjects will also have physical injuries in addition to possible radiological injuries. To best use available resources, triage information provided by conventional physical-injury triage and the measurement made by present EPR tooth-dosimeter is used by the decision-maker for the event to quickly sort (or triage) potential victims into categories of:

a. those who are unexposed or exposed below the detection threshold of the system. These should be triaged for physical injuries that may also have been sustained, and those injuries prioritized and treated appropriately.

b. those who have received detectable doses of radiation, but these doses are small enough that they will probably recover without need for treatment for acute radiation sickness. These should be triaged for physical injuries that may also have been sustained, and those injuries treated accordingly.

c. those who have received significant doses requiring conventional, conservative, treatment, for radiation sickness; which may include transfusions of blood products, prophylactic antibiotics, nursing care, and nutritional support. These should be triaged for physical injuries that may also have been sustained, and those injuries treated accordingly and consistent with their likely hospitalization for radiation sickness.

d. those who can possibly be saved by aggressive radiological-injury treatment such as bone marrow transplant. These subjects should be triaged for physical injuries that may also have been sustained, and those injuries treated if aggressive radiological injury treatment is likely to be available, and their physical injuries are not too substantial—the threshold for "black tag" from physical injuries may be somewhat lower than for those in categories a, b, or c because of high cumulative stress on their bodies; if aggressive radiological injury treatment is unlikely to be available or will be overwhelmed by patient numbers some of these patients may have to be offered comfort care. and e. those who will die despite any reasonably available treatment for their radiological injuries, and to whom hospice therapy may be offered. These subjects may also be offered comfort care, but not extensive treatment, for any physical injuries they have sustained.

In an embodiment, the dosimeter herein described is equipped with a printer for printing a radiation-dose sticker for attachment to a backside of a triage tag that is in turn attached to the subject. The front side of the triage tag is filled out with assessment, medication, and treatment information regarding other injuries the subject may have received and the appropriate tear-strips are removed. In an alternative embodiment, estimated radiation dose is printed on the sticker in both human readable form and in machine readable form as a bar-code together with patient identification information.

The coupler operates in a magnetic field of about 420 gauss with resonances at approximately 1.15 gigahertz. This embodiment may also be modified slightly in order to operate at some higher frequencies.

Since teeth are relatively dry and absorption of radio frequency energy by water is not as significant an issue as with fingernails, this embodiment also is expected to operate at 2.4 GHz with an appropriate magnetic field, and can be designed to operate at some higher frequencies—such as 9.5 GHz. Where valid data is obtained from both left and right teeth this data may be averaged to provide a more accurate measure of subject radiation exposure.

The device provides a measure of total radiation exposure of the subject since the teeth formed, which may often include some radiation exposure incurred by the subject many years before the measurement is made. The cumulative radiation dose includes radiation received from most causes such as the normal environment at 3 to 4 mSv (milisieverts—1 milisieverts is proportional to 1 milligray) per year and diagnostic X-rays at from 0.1 mSv for a chest X-ray to 10 mSv for a CT-scan, is typically well below the 2,000 millisievert (milligray) in a relatively short period of time or higher levels that require triaging into the medical system for treatment of acute radiation sickness. Therapeutic radiation to the oral cavity or neck may also have resulted in a prior exposure to teeth that would appear to be in the range of requiring acute medical treatment if received as a whole body exposure, this eventuality could be uncovered with appropriate medical history taking and by estimation of dose with EPR of fingernails in those subjects.

While the forgoing has been particularly shown and described with reference to particular embodiments thereof, it will be understood by those skilled in the art that various other changes in the form and details may be made without departing from the spirit and scope hereof. It is to be understood that various changes may be made in adapting the description to different embodiments without departing from the broader concepts disclosed herein and comprehended by the claims that follow.

What is claimed is:

1. Apparatus for performing electron paramagnetic resonance (EPR) spectrometry in teeth in vivo comprising:
   a magnet having pole plates and gap sufficiently large to permit positioning a subject's head with at least one unextracted tooth of a subject within a uniform magnetic field zone provided by the magnet;
   a device for positioning at least one resonator near the at least one unextracted tooth of the in-vivo subject;
   a coupler configured to AC-couple the resonator to a radio frequency measuring device adapted to determining an EPR spectrum;
   a processing system for computing a radiation dose based upon the EPR spectrum.

2. The apparatus of claim 1, wherein the coupler magnetically couples to the resonator.

3. The apparatus of claim 2, wherein the resonator comprises a loop and two capacitors, the loop and two capacitors formed in metal layers on a flexible printed-circuit substrate.

4. The apparatus of claim 3, wherein the magnet is adapted to be positioned at a first angle and at a second angle with respect to the subject's head, wherein the processing system is configured to obtain first EPR spectra with the magnet at the first angle and second EPR spectra with the magnet at the second angle, and to use both the first and second EPR spectra in computing the radiation dose.

5. The apparatus of claim 4, wherein the first angle and the second angle is determined by firmware of the processing system within a range of at least five degrees in either directions from an initial alignment of the head with respect to the magnet.

6. The apparatus of claim 4, wherein the magnet is adapted to be positioned such that a difference between an initial alignment of the magnet with respect to the head and the first and second angles is between three and five degrees, and a difference between the first and second angles is between three and ten degrees.

7. The apparatus of claim 4, wherein the magnet is adapted to be positioned at a third angle with respect to the subject's head, wherein the processing system is configured to obtain third EPR spectra with the magnet at the third angle, and to use the first, second, and third EPR spectra in computing the radiation dose.

8. The apparatus of claim 7, wherein a difference between the first and second angle is approximately five degrees and a difference between the first and third angle is approximately ten degrees.

9. The apparatus of claim 4, wherein the radio frequency measuring device comprises a quadrature multiple harmonic homodyne detector responsive to at least second and third harmonics.

10. The apparatus of claim 8, wherein the radio frequency measuring device operates in L-band near 1.15 GHz.

11. The apparatus of claim 4, wherein multiple EPR scans and collections of scans are acquired for a given subject and at a particular angle(s) of the magnet relative to the subject's head until further data acquisition is systematically determined to not significantly improve a precision of the dose measurement.

12. A method for estimating dose in subjects to be triaged according to radiation dose comprising:
   placing a resonator on an unextracted tooth of a subject, the resonator being magnetically coupled to a coupler attached to a radio frequency measuring device, the resonator comprising a loop and two capacitors, the resonator comprising a loop and two capacitors formed in metal layers on a flexible printed-circuit substrate;
   applying a magnetic field to the unextracted tooth of the subject by positioning a head of the subject containing the unextracted tooth between poles of a magnet;
   measuring at least one EPR spectrum of the unextracted tooth of the subject in the magnetic field by applying signals from a radio frequency source and using the radio frequency measuring device to determine responses of the unextracted tooth to the signals, the EPR spectrum being determined by sweeping either a frequency of the signals from the radio frequency source or a strength of the magnetic field; and
   using a processing system to estimate whole-body radiation dose of the subject from the measured EPR spectra, wherein the a magnet adapted to be positioned at least a first angle and at a second angle with respect to the subject's unextracted tooth, wherein the step of measuring at least one EPR spectra comprises measuring first EPR spectra with the magnet at the first angle and measuring second EPR spectra with the magnet at the second angle, and wherein estimating whole body radiation dose is performed by using both the first and second EPR spectra in computing the radiation dose.

13. The method of claim 12, wherein the magnet is adapted to be positioned at a third angle with respect to the subject's unextracted tooth, wherein the step of measuring at least one EPR spectra includes obtain third EPR spectra with the magnet at the third angle, and the step of estimating whole body radiation dose uses the first, second, and third EPR spectra in computing the radiation dose.

14. The method of claim 13, wherein the first and second angles are within a range of plus and minus five degrees from an initial alignment of magnet to the subject's unextracted tooth.

15. The method of claim 13, wherein the step of measuring at least one EPR spectra comprises using a homodyne detector responsive to at least second and third harmonics.

16. Apparatus for performing electron paramagnetic resonance (EPR) spectrometry in teeth in vivo comprising:
   a magnet having sufficient space between poles for a subject's head to be positioned between the poles;

at least one resonator having a loop and two capacitors formed in metal layers on a printed circuit substrate and adapted for placement adjacent to at least one tooth of the subject;

a radio frequency measuring device adapted for determining at least one EPR spectrum;

a processing system for computing a radiation dose based upon the EPR spectrum, and;

an apparatus for outputting the radiation dose;

the at least one resonator coupled inductively to a loop antenna the loop antenna coupled through:

a first section of high-impedance coaxial cable of length approximately one-quarter wavelength having, at a first end, a center conductor of the first section of high impedance coaxial cable coupled to the loop antenna, and at a second end the center conductor of the first section of high-impedance coaxial cable coupled to an adjustment capacitor;

a second section of high-impedance coaxial cable of length approximately three-quarter wavelength having, at a first end, a center conductor of the second section of the high impedance coaxial coupled to the loop antenna, and at a second end the center conductor of the second section of high-impedance coaxial cable coupled to the adjustment capacitor;

a third section of high-impedance coaxial cable of length approximately three-quarter wavelength having, at a first end, a center conductor of the third section of high impedance coaxial cable coupled to the adjustment capacitor, and at a second end the center conductor of the third section of high-impedance coaxial cable is coupled to a center conductor of a coaxial transmission line coupled to the radio frequency measuring device.

17. The method of claim 12 wherein the radio frequency measuring device is adapted to use multiple harmonic quadrature homodyne detection with reflection compensation responsive to at least the second and third harmonics of a frequency of the signals from the radio frequency stimulus device.

* * * * *